United States Patent
Ackley et al.

(10) Patent No.: US 6,423,271 B1
(45) Date of Patent: Jul. 23, 2002

(54) LAMINATED ASSEMBLY FOR ACTIVE BIOELECTRONIC DEVICES

(75) Inventors: Donald E. Ackley, Cardiff; Thomas R. Jackson, La Jolla; Edward L. Sheldon, III, San Diego, all of CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

(21) Appl. No.: 09/527,069

(22) Filed: Mar. 16, 2000

Related U.S. Application Data

(63) Continuation of application No. 08/753,962, filed on Dec. 4, 1996, now Pat. No. 6,287,517, and a continuation-in-part of application No. 08/709,358, filed on Sep. 6, 1996, now Pat. No. 6,129,828, which is a continuation-in-part of application No. 08/534,454, filed on Sep. 27, 1995, now Pat. No. 5,849,486, which is a continuation-in-part of application No. 08/304,657, filed on Sep. 9, 1994, now Pat. No. 5,632,957, which is a continuation-in-part of application No. 08/271,882, filed on Jul. 7, 1994, now Pat. No. 6,017,696, which is a continuation-in-part of application No. 08/146,504, filed on Nov. 1, 1993, now Pat. No. 5,605,662.

(51) Int. Cl.⁷ .......................... G01N 15/00; G01N 1/00
(52) U.S. Cl. ...................................... 422/68.1; 422/50
(58) Field of Search ...................... 422/50, 68.1; 435/6, 435/91.1, 91.2

(56) References Cited

U.S. PATENT DOCUMENTS

| | | | |
|---|---|---|---|
| 3,950,738 A | 4/1976 | Hayashi et al. | 340/173 LS |
| 3,995,190 A | 11/1976 | Salgo | 313/391 |
| 4,563,419 A | 1/1986 | Ranki et al. | 435/6 |

(List continued on next page.)

FOREIGN PATENT DOCUMENTS

| | | |
|---|---|---|
| EP | 0228075 | 7/1987 |
| GB | 2156074 | 10/1985 |
| JP | 05317030 | 3/1993 |
| WO | 8603782 | 7/1986 |
| WO | WO 88/08528 | 11/1988 |
| WO | WO 89/01159 | 2/1989 |
| WO | 8910977 | 11/1989 |
| WO | 9001564 | 2/1990 |
| WO | WO 92/04470 | 3/1992 |
| WO | WO 93/22678 | 11/1993 |
| WO | WO 95/01159 | 1/1995 |
| WO | WO 95/07363 | 3/1995 |
| WO | WO 96/07917 | 3/1996 |
| WO | WO 96/14509 | 5/1996 |
| YU | 57087 | 8/1990 |

OTHER PUBLICATIONS

Anand and Southern "Pulsed Field Gel Electrophoresis," Gel Electrophoresis of Nucleic Acids—A Practical Approach, 2d. Ed., D. Rickwood and B.D. Hames (New York:IRL Press, 1990) pp. 101–123.

Anderson and Young, "Quantitative Filter Hybridization," Nucleic Acid Hybridization—A Practical Approach, Eds. B.D. Hames and S.J. Higgins (Washington, D.C . :IRL Press 1985) pp. 73–11.

(List continued on next page.)

Primary Examiner—Ardin H. Marschel
(74) Attorney, Agent, or Firm—Lyon & Lyon LLP

(57) ABSTRACT

A multilayer, laminated device for performing fluidic operations includes a first exterior support layer, an adjacent layer disposed in laminated relationship with a portion of the exterior support layer, a second exterior support layer disposed in laminated relationship with a portion of the adjacent layer, and a fluidic pump that is disposed in the adjacent layer. The fluidic pump includes a first gear rotationally mounted to the adjacent layer, the first gear having a magnet contained therein. A second gear is rotationally mounted to the adjacent layer, the second gear having a magnet contained therein, the second gear being engaged with the first gear in a meshed relationship.

5 Claims, 5 Drawing Sheets

U.S. PATENT DOCUMENTS

| | | | |
|---|---|---|---|
| 4,580,895 A | 4/1986 | Patel | 356/39 |
| 4,584,075 A | 4/1986 | Goldstein et al. | 204/182.3 |
| 4,594,135 A | 6/1986 | Goldstein | 204/180.1 |
| 4,751,177 A | 6/1988 | Stabinsky | 435/6 |
| 4,787,963 A | 11/1988 | MacConnell | 204/180.1 |
| 4,816,418 A | 3/1989 | Mack et al. | 436/518 |
| 4,822,566 A | 4/1989 | Newman | 422/68 |
| 4,908,112 A | 3/1990 | Pace | 204/299 R |
| 5,063,081 A | 11/1991 | Cozzette et al. | 427/2 |
| 5,075,077 A | 12/1991 | Durley, III et al. | 422/56 |
| 5,096,807 A | 3/1992 | Leaback | 435/6 |
| 5,125,748 A | 6/1992 | Bjornson et al. | 356/414 |
| 5,126,022 A | 6/1992 | Soane et al. | 204/180.1 |
| 5,143,854 A | 9/1992 | Pirrung et al. | 436/518 |
| 5,164,319 A | 11/1992 | Hafeman et al. | 435/291 |
| 5,166,063 A | 11/1992 | Johnson | 435/173 |
| 5,200,051 A | 4/1993 | Cozzette et al. | 204/403 |
| 5,202,231 A | 4/1993 | Drmanac et al. | 435/6 |
| 5,219,726 A | 6/1993 | Evans | 435/6 |
| 5,227,265 A | 7/1993 | DeBoer et al. | 430/41 |
| 5,229,297 A * | 7/1993 | Schnipelsky et al. | 436/94 |
| 5,234,566 A | 8/1993 | Osman et al. | 204/403 |
| 5,304,487 A | 4/1994 | Wilding et al. | 435/291 |
| 5,312,527 A | 5/1994 | Mikkelsen et al. | 204/153.12 |
| 5,393,401 A | 2/1995 | Knoll | 204/418 |
| 5,434,049 A | 7/1995 | Okano et al. | 435/6 |
| 5,436,129 A * | 7/1995 | Stipleton | 435/6 |
| 5,856,174 A * | 1/1999 | Lipshutz et al. | 435/286.5 |

OTHER PUBLICATIONS

Baines, "Setting a Sequence to Sequence a Sequence," Bio/Technology, 10:757–758 (1992).

Barinaga, "Will 'DNA Chip' Speed Genome Initiative," Science, 253:1489 (1991).

Beattie et al., "Genosensor Technology," The 1992 San Diego Conference: Genetic Recognition, pp. 1–5 (Nov. 1992).

Beltz et al., "Isolation of Multigene Families and Determination of Homologies by Filter Hybridization Methods," Methods of Enzymology, 100:266–285 (1983).

Connor et al., "Detection of Sickle Cell $\beta^3$–Globin Allele by Hybridization with Synthetic Oligonucleotides," Proc. Nat'l. Acad. Sci. USA, 80:278–282 (1983).

Drmanac et al., "Sequencing of Megabase Plus DNA by Hybridization: Theory of the Method," Genomics, 4:114–128 (1989).

Drmanac et al., "DNA Sequencing Determination by Hybridixation: A Strategy for Efficient Large–Scale Sequencing," Science, 260; 1649–1652 (1993).

Fodor et al., "Multiplexed Biochemical Assays with Biological Chips," Nature, 364:555–556 (1993).

Fodor et al., "Light–Directed, Spatially Addressable Parallel Chemical Synthesis," 251:767–773 (1992).

Horejsi, "Some Theoretical Aspects of Affinity Electrophoresis," Journal of Chromatography, 178:1–13 (1979).

Horejsi et al., Determination of Dissociation Constants of Lectin Sugar Complexes by Means of Affinity Elecrophoresis, Biochimica at Biophysica Acta, 499:200–300 (1977).

Ranki et al., "Sandwich Hybridization as a Convenient Method for the Detection of Nucleic Acids in Crude Samples," Gene, 21:77–85 (1983).

Saiki, "Amplification of Genomic DNA," PCR Protocols: A Guide to Methods and Applications, (Academic Press, Inc., 1990) pp. 13–20.

Southern et al., "Analyzing and Comparing Nucleic Acid Sequences by Hybridization to Arrays of Oligonucleotides Evaluation Using Experimental Models," Genomics, 13:1008–1017 (1992).

Strezoska et al., "DNA Sequencing by Hybridization: 100 Bases Read by a Nongel Based Method," Proc. Nat'l. Acad. Sci. USA., 88:10089–93 (1991).

Wallace et al., "Hybridization of Synthetic Oligodcoxyribonucleotides to $\phi \times 174$ DNA: The Effect of Single Base Pair Mismatch," Nucleic Acid Res., 6:3543–3557 (1979).

Washizu, "Electrostatic Manipulation of Biological Objects," Journal of Electrostatics, 25:109–123 (1990).

Washizu and Kurosawa, "Electrostatic Manipulation of DNA in Microfabricated Structures," IEEE Transactions on Industry Applications, 26:1165–1172 (1990).

Brown et al. "Electrochemically Induced Absorption of Radio–Labeled DNA on Gold and HOPG Substrates for STM Investigations," Ultramicroscopy, 38 (1991) pp. 253–264.

Palacek, "New Trends in Electrochemical Analysis of Nucleic Acids," Bioelectrochemistry and Bioenergentics, 20 (1988) pp. 179–194.

Kensall D. Wiise et al., Microelectromechanical Systems in Japan, Japanese Technology Evaluation Center, Sep. 1994, WTEC Hyper–Librarian.

* cited by examiner

LAMINATED ASSEMBLY FOR ACTIVE BIOELECTRONIC DEVICES

RELATED APPLICATION INFORMATION

This application is a continuation of application Ser. No. 08/753,962, filed on Dec. 4, 1996, now U.S. Pat. No. 6,287,517; entitled "Laminated Assembly for Active Bioelectronic Devices," which is a continuation-in-part of application Ser. No. 08/534,454, filed on Sep. 27, 1995, entitled "Apparatus and Methods for Active Programmable Matrix Devices," now U.S. Pat. No. 5,849,486, which is a continuation-in-part of application Ser. No. 08/304,657, filed on Sep. 9, 1994, entitled, as amended, "Molecular Biological Diagnostic Systems Including Electrodes," now U.S. Pat. No. 5,632,957, which is a continuation-in-part of application Ser. No. 08/271,882, filed on Jul. 7, 1994, entitled, as amended, "Methods for Electronic Stringency Control for Molecular Biological Analysis and Diagnostics," now U.S. Pat. No. 6,017,696, which is a continuation-in-part of application Ser. No. 08/146,504, filed on Nov. 1, 1993, entitled, as amended, "Active Programmable Electronic Devices for Molecular Biological Analysis and Diagnostics," now U.S. Pat. No. 5,605,662, and application Ser. No. 08/709,358, filed on Sep. 6, 1996, now U.S. Pat. No. 6,129,828; entitled "Apparatus and Methods for Active Biological Sample Preparation." The priority of these prior applications is expressly claimed and their disclosure is hereby incorporated by reference in their entirety.

FIELD OF THE INVENTION

This invention relates to methods of manufacture and devices useful in performing active biological operations. More particularly, the invention relates to devices containing active electrodes especially adapted for electrophoretic transport of nucleic acids, their hybridization and analysis.

BACKGROUND OF THE INVENTION

Molecular biology comprises a wide variety of techniques for the analysis of nucleic acid and protein. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e.g., J. Sambrook, E. F. Fritsch, and T. Maniatis, *Molecular Cloning: A Laboratory Manual,* 2 Ed., Cold spring Harbor Laboratory Press, Cold Spring Harbor, N.Y., 1989).

Most of these techniques involve carrying out numerous operations (e.g., pipetting, centrifugations, electrophoresis) on a large number of samples. They are often complex and time consuming, and generally require a high degree of accuracy. Many a technique is limited in its application by a lack of sensitivity, specificity, or reproducibility. For example, these problems have limited many diagnostic applications of nucleic acid hybridization analysis.

The complete process for carrying out a DNA hybridization analysis for a genetic or infectious disease is very involved. Broadly speaking, the complete process may be divided into a number of steps and substeps (see FIG. 1). In the case of genetic disease diagnosis, the first step involves obtaining the sample (blood or tissue). Depending on the type of sample, various pre-treatments would be carried out. The second step involves disrupting or lysing the cells, which then release the crude DNA material along with other cellular constituents. Generally, several sub-steps are necessary to remove cell debris and to purify further the crude DNA. At this point several options exist for further processing and analysis. One option involves denaturing the purified sample DNA and carrying out a direct hybridization analysis in one of many formats (dot blot, microbead, microplate, etc.). A second option, called Southern blot hybridization, involves cleaving the DNA with restriction enzymes, separating the DNA fragments on an electrophoretic gel, blotting to a membrane filter, and then hybridizing the blot with specific DNA probe sequences. This procedure effectively reduces the complexity of the genomic DNA sample, and thereby helps to improve the hybridization specificity and sensitivity. Unfortunately, this procedure is long and arduous. A third option is to carry out the polymerase chain reaction (PCR) or other amplification procedure. The PCR procedure amplifies (increases) the number of target DNA sequences relative to non-target sequences. Amplification of target DNA helps to overcome problems related to complexity and sensitivity in genomic DNA analysis. All these procedures are time consuming, relatively complicated, and add significantly to the cost of a diagnostic test. After these sample preparation and DNA processing steps, the actual hybridization reaction is performed. Finally, detection and data analysis convert the hybridization event into an analytical result.

The steps of sample preparation and processing have typically been performed separate and apart from the other main steps of hybridization and detection and analysis. Indeed, the various substeps comprising sample preparation and DNA processing have often been performed as a discrete operation separate and apart from the other substeps. Considering these substeps in more detail, samples have been obtained through any number of means, such as obtaining of full blood, tissue, or other biological fluid samples. In the case of blood, the sample is processed to remove red blood cells and retain the desired nucleated (white) cells. This process is usually carried out by density gradient centrifugation. Cell disruption or lysis is then carried out on the nucleated cells to release DNA, preferably by the technique of sonication, freeze/thawing, or by addition of lysing reagents. Crude DNA is then separated from the cellular debris by a centrifugation step. Prior to hybridization, double-stranded DNA is denatured into single-stranded form. Denaturation of the double-stranded DNA has generally been performed by the techniques involving heating (>Tm), changing salt concentration, addition of base (NaOH), or denaturing reagents (urea, formamide, etc.). Workers have suggested denaturing DNA into its single-stranded form in an electrochemical cell. The theory is stated to be that there is electron transfer to the DNA at the interface of an electrode, which effectively weakens the double-stranded structure and results in separation of the strands. See, generally, Stanley, "DNA Denaturation by an Electric Potential," U.K. patent application 2,247,889 published Mar. 18, 1992.

Nucleic acid hybridization analysis generally involves the detection of a very small number of specific target nucleic acids (DNA or RNA) with an excess of probe DNA, among a relatively large amount of complex non-target nucleic acids. The substeps of DNA complexity reduction in sample preparation have been utilized to help detect low copy numbers (i.e., 10,000 to 100,000) of nucleic acid targets. DNA complexity is overcome to some degree by amplification of target nucleic acid sequences using polymerase chain reaction (PCR). (See, M. A. Innis et al, *PCR Protocols: A Guide to Methods and Applications,* Academic Press, 1990). While amplification results in an enormous number of target nucleic acid sequences that improves the subsequent direct probe hybridization step, amplification involves lengthy and cumbersome procedures that typically must be performed on a stand alone basis relative to the other substeps. Substantially complicated and relatively large equipment is required to perform the amplification step.

The actual hybridization reaction represents the most important and central step in the whole process. The hybridization step involves placing the prepared DNA sample in contact with a specific reporter probe, at a set of optimal conditions for hybridization to occur to the target DNA sequence. Hybridization may be performed in any one of a number of formats. For example, multiple sample nucleic acid hybridization analysis has been conducted on a variety of filter and solid support formats (See G. A. Beltz et al., in *Methods in Enzymology,* Vol. 100, Part B, R. Wu, L. Grossman, K. Moldave, Eds., Academic Press, New York, Chapter 19, pp. 266–308, 1985). One format, the so-called "dot blot" hybridization, involves the non-covalent attachment of target DNAs to filter, which are subsequently hybridized with a radioisotope labeled probe(s). "Dot blot" hybridization gained wide-spread use, and many versions were developed (see M. L. M. Anderson and B. D. Young, in *Nucleic Acid Hybridization—A Practical Approach,* B. D. Hames and S. J. Higgins, Eds., IRL Press, Washington, D.C. Chapter 4, pp. 73–111, 1985). It has been developed for multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

New techniques are being developed for carrying out multiple sample nucleic acid hybridization analysis on micro-formatted multiplex or matrix devices (e.g., DNA chips) (see M. Baringa, 253 Science, pp.1489, 1991; W. Bains, 10 Bio/Technology, pp. 757–758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

The micro-formatted hybridization can be used to carry out "sequencing by hybridization" (SBH) (see M. Baringa, 253 Science, pp. 1489, 1991; W. Bains, 10 Bio/Technology, pp. 757–758, 1992). SBH makes use of all possible n-nucleotide oligomers (n-mers) to identify n-mers in an unknown DNA sample, which are subsequently aligned by algorithm analysis to produce the DNA sequence (R. Drmanac and R. Crkvenjakov, Yugoslav Patent Application #570/87, 1987; R. Drmanac et al., 4 Genomics, 114, 1989; Strezoska et al., 88 Proc. Natl. Acad. Sci. USA 10089, 1992; and R. Drmanac and R. B. Crkvenjakov, U.S. Pat. No. 5,202,231, Apr. 13, 1993).

There are two formats for carrying out SBH. The first format involves creating an array of all possible n-mers on a support, which is then hybridized with the target sequence. The second format involves attaching the target sequence to a support, which is sequentially probed with all possible n-mers. Both formats have the fundamental problems of direct probe hybridizations and additional difficulties related to multiplex hybridizations.

Southern, United Kingdom Patent Application GB 8810400, 1988; E. M. Southern et al., 13 Genomics 1008, 1992, proposed using the first format to analyze or sequence DNA. Southern identified a known single point mutation using PCR amplified genomic DNA. Southern also described a method for synthesizing an array of oligonucleotides on a solid support for SBH. However, Southern did not address how to achieve optimal stringency condition for each oligonucleotide on an array.

Concurrently, Drmanac et al., 260 Science 1649–1652, 1993, used the second format to sequence several short (116 bp) DNA sequences. Target DNAs were attached to membrane supports ("dot blot" format). Each filter was sequentially hybridized with 272 labeled 10-mer and 11-mer oligonucleotides. A wide range of stringency condition was used to achieve specific hybridization for each n-mer probe; washing times varied from 5 minutes to overnight, and temperatures from 0 C. to 16 C. Most probes required 3 hours of washing at 16 C. The filters had to be exposed for 2 to 18 hours in order to detect hybridization signals. The overall false positive hybridization rate was 5% in spite of the simple target sequences, the reduced set of oligomer probes, and the use of the most stringent conditions available.

A variety of methods exist for detection and analysis of the hybridization events. Depending on the reporter group (fluorophore, enzyme, radioisotope, etc.) used to label the DNA probe, detection and analysis are carried out fluorimetrically, colorimetrically, or by autoradiography. By observing and measuring emitted radiation, such as fluorescent radiation or particle emission, information may be obtained about the hybridization events. Even when detection methods have very high intrinsic sensitivity, detection of hybridization events is difficult because of the background presence of non-specifically bound materials. A number of other factors also reduce the sensitivity and selectivity of DNA hybridization assays.

In conventional fluorimetric detection systems, an excitation energy of one wavelength is delivered to the region of interest and energy of a different wavelength is remitted and detected. Large scale systems, generally those having a region of interest of two millimeters or greater, have been manufactured in which the quality of the overall system is not inherently limited by the size requirements of the optical elements or the ability to place them in optical proximity to the region of interest. However, with small geometries, such as those below 2 millimeters, and especially those on the order of 500 microns or less in size of the region of interest, the conventional approaches to fluorimeter design have proved inadequate. Generally, the excitation and emission optical elements must be placed close to the region of interest. Preferably, a focused spot size is relatively small, often requiring sophisticated optical designs. Further, because it is usually desirable to maximize the detectable area, the size of the optical components required to achieve these goals in relation to their distance from the region of interest becomes important, and in many cases, compromises the performance obtained. Accordingly, a need exists for an improved fluorescent detection system.

Attempts have been made to combine certain processing steps or substeps together. For example, various microrobotic systems have been proposed for preparing arrays of DNA probe on a support material. For example, Beattie et al., in *The 1992 San Diego Conference: Genetic Recognition,* November 1992, used a microrobotic system to deposit micro-droplets containing specific DNA sequences into individual microfabricated sample wells on a glass substrate.

Generally, the prior art processes have been extremely labor and time intensive. For example, the PCR amplification process is time consuming and adds cost to the diagnostic assay. Multiple steps requiring human intervention either during the process or between processes is suboptimal in that there is a possibility of contamination and operator error. Further, the use of multiple machines or complicated robotic systems for performing the individual processes is often prohibitive except for the largest laboratories, both in terms of the expense and physical space requirements.

As is apparent from the preceding discussion, numerous attempts have been made to provide effective techniques to conduct multi-step, multiplex molecular biological reactions. However, for the reasons stated above, these techniques are "piece-meal" and limited. These various approaches are not easily combined to form a system which can carry out a complete DNA diagnostic assay. Despite the long recognized need for such a system, no satisfactory solution has been proposed previously.

SUMMARY OF THE INVENTION

Methods of manufacture and apparatus adapted for advantageous use in active electronic devices utilized for biological diagnostics are disclosed. In the preferred embodiment, a multilayer, laminated device includes at least a first planar sample support, the planar sample support including a through hole, a planar electrode adjacent the planar sample support, the electrode including a through region, and a second planar support including a vent through hole, the planar electrode being in a laminated relationship between the first planar sample support and the second planar support, further characterized in that the sample through hole, electrode through region and vent through hole overlap one another. In the preferred embodiment, the planar support members may be formed of a thin, sheet-like material, most preferably a polyimide sheet such as DuPont Kapton. The preferred thickness of a planar support is in the range from 1 to 5 mils. The planar sample support material is advantageously selected to have properties consistent with the goals and purposes of the active biological device, for example, exhibiting low binding properties for DNA, having low inherent fluorescence, being relatively inert in an acidic environment and being nonconducting.

Stacked or laminated structures may be formed through the use of multiple sheets. In one preferred embodiment, one or more additional layers are disposed above the planar sample support in a direction towards the surface, which will receive the biological material. Similarly, a multilayer or laminated structure may be formed beneath the second planar support. The additional laminated layers would typically include through holes, which preferably would be aligned with the remaining through holes or regions. Multilayer or laminated structures may be advantageously formed in numerous configurations. In one embodiment, electrodes may be disposed at differing depths relative to the sample side of the laminated device such that different offset distances between the electrode and the sample applied to the device are achieved. In this way, the different offset distances permit optimization of various functions, such as where complexity reduction and assaying are performed on the same device. Electrodes may be formed at different levels such as through use of an intervening planar support disposed between a first electrode and a second electrode at different levels.

In one aspect of this invention, the lateral dimension of the through hole of the first planar sample support is different than the lateral width of the vent through hole of the second planar support. In one embodiment, the lateral dimensions of the vent through hole are larger than the lateral dimensions of the sample through hole. Preferably, a permeation layer is included in the sample through hole and at least a portion of the vent through hole. Relative advantages of this embodiment potentially include the advantageous venting of gas from reactions at or near the planar electrode through a region separate from the hybridization reaction, and the ability of this structure to lock in a permeation layer disposed in the sample through hole, electrode through region and at least a portion of the vent through hole. An alternative embodiment has a sample through hole with a lateral dimension, which is greater than the lateral dimension of the vent through hole. The planar electrode includes at least a portion oriented to face outward through the sample through hole.

In another aspect of this invention, fluidic devices may be formed on, within, or adjacent to the laminated structures. For example, a pump, such as a magnetically driven microminiature pump may be included within the laminated structure. Fluids may be pumped or moved through the system in such a manner.

In yet another aspect of this invention, chip-on flexible circuit technology may be employed to hybridize electronic circuitry in operative contact with the active biological device. Further, multiple level interconnections may be formed, such as through use of vias connecting between one or more layers. In the preferred embodiment, these vias may be exposed to external of the device through the second planar support, rather than through the uppermost planar sample support which adapted to receive biological materials.

The laminated circuit structures and methods of this invention are advantageously utilized in forming active biological devices. A device having a combination of biological complexity reduction and diagnostic assay, as well as counter electrodes may be formed on a single device.

In yet another aspect of this invention, a multilayer, laminated structure may be utilized to perform biological amplification processes, especially polymerase chain reaction (PCR). Optionally, one or more heaters may be integrated into or formed adjacent the laminated structure to aid in the amplification process.

Accordingly, it is an object of this invention to provide an active biological device having reduced costs of manufacture yet consistent with achieving a small size microlocation.

It is yet another object of this invention to provide a device having a high degree of uniformity of exposed electrode from microlocation to microlocation, as well as device to device.

It is yet a further object of this invention to provide a active biological device having reduced bubbling and reduced burn-out.

It is yet another object of this invention to provide an active biological device having improved gas venting and buffering capacity.

DETAILED DESCRIPTION OF THE INVENTION

Figure 1A:
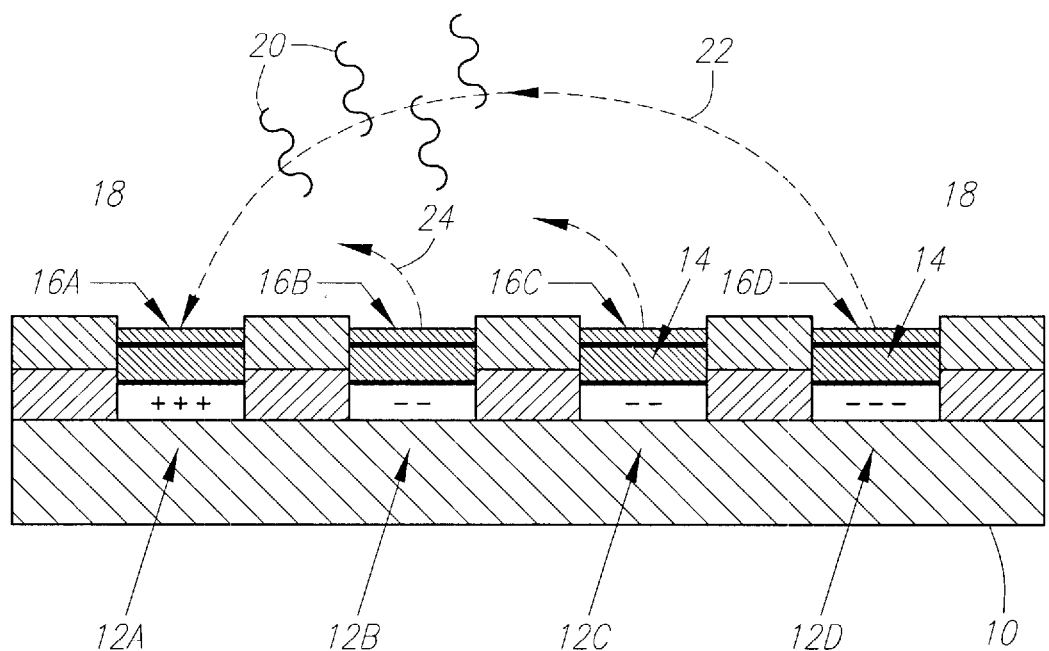
FIGS. 1A and 1B show an active, programmable electronic matrix device (APEX) in cross-section (FIG. 1A) and in perspective view (FIG. 1B).
Figure 1B:
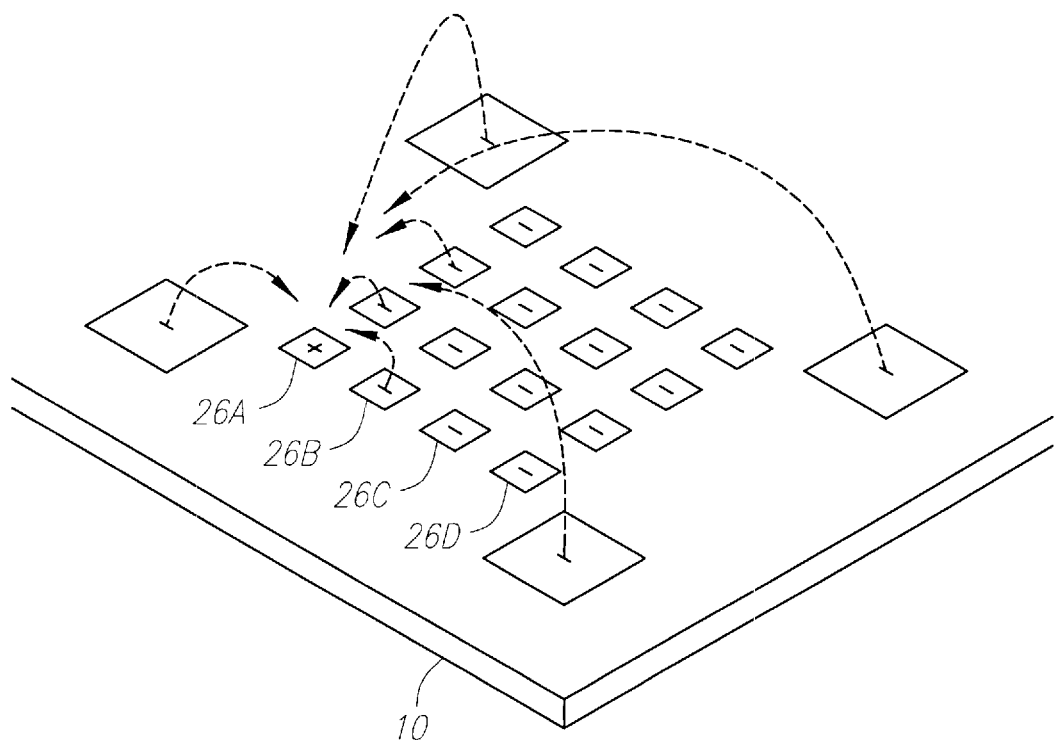

FIGS. 1A and 1B illustrate a simplified version of the active programmable electronic matrix hybridization system for use with this invention. Generally, a substrate 10 supports a matrix or array of electronically addressable microlocations 12. For ease of explanation, the various microlocations in FIG. 1A have been labeled 12A, 12B, 12C, and 12D. A permeation layer 14 is disposed above the individual electrodes 12. The permeation layer permits transport of relatively small charged entities through it, but limits the mobility of large charged entities, such as DNA, to keep the large charged entities from easily contacting the electrodes 12 directly during the duration of the test. The permeation layer 14 reduces the electrochemical degradation which would occur in the DNA by direct contact with the electrodes 12, possibility due, in part, to extreme pH resulting from the electrolytic reaction. It further serves to minimize the strong, non-specific adsorption of DNA to electrodes. Attachment regions 16 are disposed upon the permeation layer 14 and provide for specific binding sites for target materials. The attachment regions 16 have been labeled 16A, 16B, 16C, and 16D to correspond with the identification of the electrodes 12A–D, respectively.

In operation, reservoir 18 comprises that space above the attachment regions 16 that contains the desired, as well as undesired, materials for detection, analysis or use. Charged entities 20, such as charged DNA are located within the reservoir 18. In one aspect of this invention, the active, programmable, matrix system comprises a method for transporting the charged material 20 to any of the specific microlocations 12. When activated, a microlocation 12 generates the free field electrophoretic transport of any charged functionalized specific binding entity 20 towards the electrode 12. For example, if the electrode 12A were made positive and the electrode 12D negative, electrophoretic lines of force 22 would run between the electrodes 12A and 12D. The lines of electrophoretic force 22 cause transport of charged binding entities 20 that have a net negative charge toward the positive electrode 12A. Charged materials 20 having a net positive charge move under the electrophoretic force toward the negatively charged electrode 12D. When the net negatively charged binding entity 20 that has been functionalized contacts the attachment layer 16A as a result of its movement under the electrophoretic force, the functionalized specific binding entity 20 becomes covalently attached to the attachment layer 16A.

Figure 2:
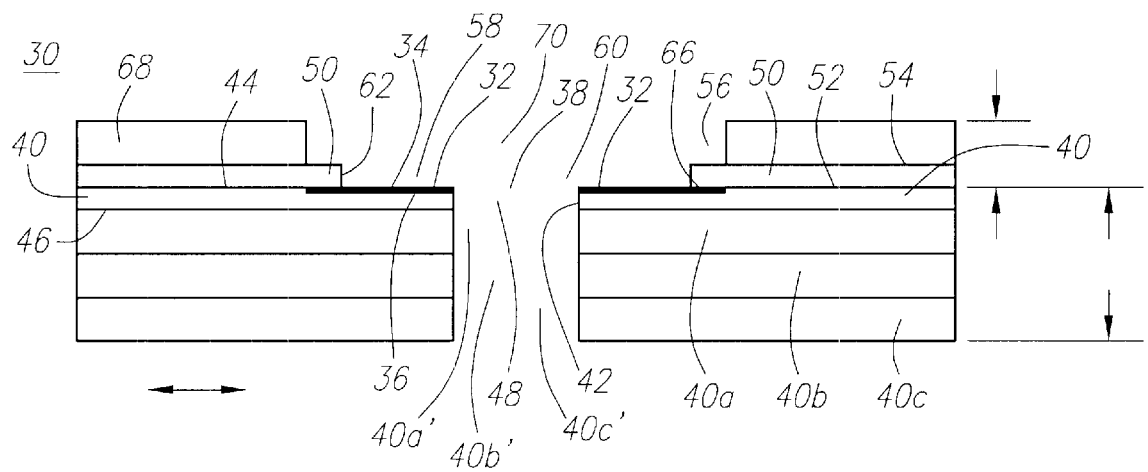
FIG. 2 is a cross-sectional view of a multilayer structure including the electrode in a sample facing orientation.

FIG. 2 is a cross-sectional diagram of a laminated structure 30 according to one embodiment of this invention. An electrode 32 preferably has a generally sheet-like or planar structure at least at certain portions of the electrode 32. The electrode 32 includes an upper surface 34 and lower surface 36. An electrode through region 38 is located in the electrode 32. In the preferred embodiment, the electrode through region 38 is a hole, that is, the electrode 32 completely circumscribes the electrode through region 38. However, the electrode through region 38 need not be formed as a hole, and may only be bounded by or partially surrounded by the electrode 32, or may be set back from the hole as in an annulus.

A planar support 40 is preferably formed of a sheet-like material. The planar support 40 includes an upper surface 44 and a lower surface 46, those surfaces generally being parallel to one another. The planar support 40 further includes a through hole 48, defined at least in part by edge 42, also known as a vent through hole in that the through hole 48 is adapted to permit gas, which may form, for example, through electrochemical reactions at or near the electrode 32, to be vented from the laminated structure 30.

A planar support 50 includes a lower surface 52 and an upper surface 54. Again, the planar sample support 50 preferably is of a sheet-like material having lateral extension which is significantly (at least 10:1 times) greater than the thickness of the sample support 50. The planar sample support 50 includes a sample through hole 56, which is preferably continuous around its perimeter.

The electrode 32 is laminated or sandwiched between the planar sample support 50 and the planar support 40. Ideally, the sample through hole 56, electrode through region 38 and vent through hole 48 overlap, and most preferably are aligned when of substantially the same shape and lateral width. The lateral widths refer to measurements in the direction of the two-headed arrow in FIG. 2, namely, within the plane of the sheet. A well 58 is defined by the interior edges 62 of the planar sample support 50, and the upper surface 64 of the electrode 32. Preferably, the interior edge 62 of the planar sample support 50 overlaps at region 66 to form a better seal between the upper surface 34 of the electrode 32 and the lower surface 52 of the planar sample support 50.

Optionally, one or more additional layers may be laminated or otherwise affixed to the structure described previously. For example, additional planar support layers 40a, 40b and 40c may be disposed beneath the planar support 40. Preferably, through holes 40a', 40b', and 40c' are arranged in overlapping relationship with the vent through hole 48, and most preferably aligned thereto. Similarly, one or more additional sample support structures 68 may be disposed on, and preferably laminated to, the planar sample support 50. Again, a sample through hole 70, having a lateral dimension which is greater than or equal to the lateral dimension of the sample through hole 56 is preferred.

A permeation layer is disposed within at least the well 58. Optionally, the permeation layer may fill the permeation region 60 which may preferably terminate at the upper surface of the upper most sample support 68, which may also be termed an external sample support in that it provides a surface exposed to the sample materials.

The preferred sheet-like material for structures, e.g., the planar support 40 and planar sample support 50 is polyimide. One source for sheet polyimide is DuPont who sells materials generally ranging from 1 to 5 mils thick under the trademark Kapton. Generally, it is desired that these materials have relatively low swelling (preferably less than 10%, more preferably less than 5% and most preferably less than 2%) in the presence of fluids, preferably have relatively low inherent fluorescence, are substantially inert in an acidic environment (most preferably to a pH of 2 and more preferably to a pH of 1), are electrically insulative or nonconducting. Utilizing currently available materials, relatively thin, e.g., 1 mil thickness sheets, may be patterned with 1 mil wide lines and 1 mil wide spaces.

As shown in FIG. 2, multiple sheets may be laminated together to form composite structures. In the exemplary structure of FIG. 2, the planar support 40 and planar sample support 50 are 1 mil thick, the planar supports 40a, 40b, and 40c are 5 mils thick and the external contact layer 68 is 2 mils thick. Generally, the use of multiple sample supports 50, 68 above (i.e., towards the side of the laminated structure 30 adapted to receive the sample) a well 58 may be built. As shown in FIG. 2, the electrode 32 is at the bottom of a well, which is approximately 5 to 6 mils below the upper surface of the sample support 68 (See the opposed arrows in FIG. 2). Adhesive disposed between the various sample support layers increases the well depth, typically approximately one mil per layer of adhesive. As shown in FIG. 2, the overall laminated structure 30 has a thickness approximately 25 mils (See the oppositely directed arrows in FIG. 2). Laminated structures 30 having thicknesses up to 200 mils or being as thin as 2 mils may be fabricated using conventional technologies.

While polyimide is the preferred material, other materials meeting one or more of the criteria include: polymethylmethacrylate (PMMA), polytetrafluorethylene (PTFE-Teflon), polyester (Mylar), polystyrene, polycarbonate, and like materials. Further, various layers in the laminated structure 30 may be selected from different materials to optimize the performance of that layer or the laminate structure 30. For example, the exposed surface of the external sample support 68 may optionally be selected for low adhesion to biological materials. The support 68 may be chosen for its inherent low specific binding with biological materials or the surface of the sample support 68 may be altered to that purpose. One or more layers, especially the external or contact sample support 68 layer may be chosen for high reflectivity, low reflectivity (such as through the use of black or absorbing materials), having a desired texture (e.g., low texture for bonding purposes and surface chemistry optimization), or have hydrophobic or hydrophilic properties. Preferably, the sample support layers, the planar support 40 and the optional sample support 68, are nonporous. The laminated structure 30 is generally preferred to be impermeable to fluids, such as water.

The electrode 32 is preferably formed on or integral to a sheet, such as a polyimide sheet, such as the planar support 40 of FIG. 2. The electrode materials are preferably noble metals, most preferably gold. Generally, it is preferred that no base metals which would adversely affect biological materials to be supplied to the laminated structure 30, such as DNA, are exposed in the electrode 32. Most preferably, it is desirable to avoid copper and iron, and to a lesser extent lead and tin in the materials, or at least, avoiding the exposure of those materials or their ions if present to the biological materials. The electrode 30 should be formed from a material, and result in a structure, which is generally noncorrosive, is bondable, adheres to other materials, serves to minimize or avoid leakage currents, generates relatively low amounts of electrochemistry, and has a relatively high electrochemical voltage at which the surface of the electrode emits constituents materials. Other desirable electrodes may be formed from nichrome, platinum, nickel, stainless steel or indium tin oxide (ITO), ITO being advantageously used when optical detection, especially from the vent side, is utilized. In the preferred embodiment, when polyimide sheets are utilized, the preferred adhesive is DuPont acrylic adhesive, or polyester adhesive. Generally, it is desirable that the adhesive have low squeeze out properties such that during the lamination process, excessive amounts of adhesive do not exit such as at the interior edge 62 of the planar sample support 50, lest excessive, and unpredictable, amounts of adhesive reside on the upper surface 64 of the electrode 32. Generally, the adhesive is on the order of 1 mil thick.

Figure 3:
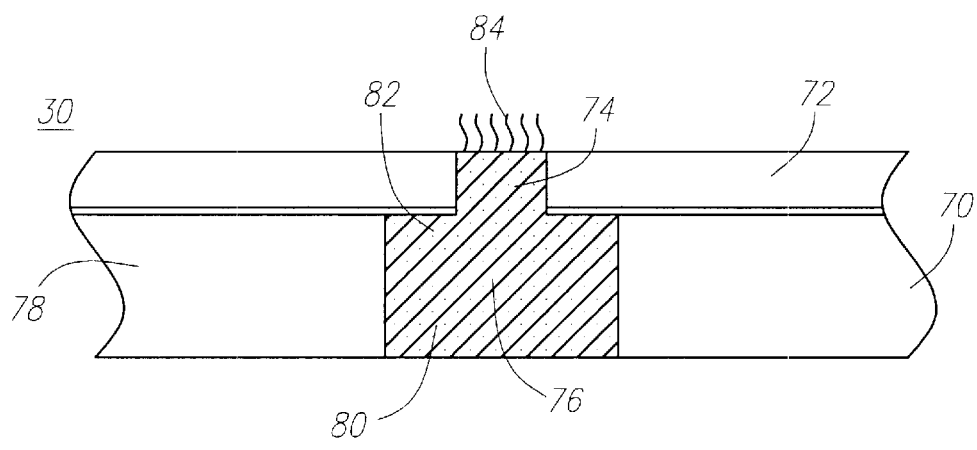
FIG. 3 is a cross-sectional view of a multilayer structure having a vent hole with a lateral dimension greater than the sample through hole.

FIG. 3 is a cross-sectional view of a laminated structure 30 in which the electrode 70 is disposed on the underside, namely, facing away from the side of the laminated structure 30 adapted to receive the sample, on the sample support 72 (or other laminated supports). A sample through hole 74 and electrode through region 76 preferably have the same lateral dimension and are in overlapping, most preferably aligned, relationship. A planar support 78 includes a vent hole 80, again the vent hole 80 being an overlapping relationship, most preferably concentric aligned relationship, with the sample through hole 74 and electrode through region 76. The planar electrode 70 is in a laminated relationship between the sample support 72 and the planar support 78.

FIG. 3 shows the presence of a permeation layer or permeable polymer 82, which was omitted for drawing clarity, though described, in connection with FIG. 2. Additionally, capture probes 84 are disposed on the sample side of the laminated structure 30 at the sample side at the permeable polymer 82.

Figure 4:
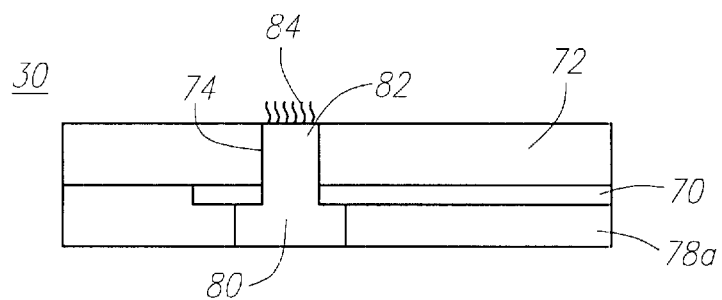
FIG. 4 is a cross-sectional view of a multilayer device having a vent hole with a lateral dimension which is greater than the lateral dimension of the sample through hole.

FIG. 4 shows a cross-sectional view of a laminated structure 30, which differs from FIG. 3 in the thickness of the planar support 78. Whereas planar support 78 in FIG. 3 is relatively thick, preferably at least twice, more preferably three times and most preferably substantially five times, as thick as the sample support 72, the structure of FIG. 4 has substantially equal thickness of sample support 72 and planar support 78A.

Each of the laminated structures 30 of FIG. 3 and FIG. 4 have a relatively larger volume comprising the vent hole 80 in comparison to the volume of the sample through hole 74. Preferably, the relative sizing of the vent hole 80 to the volume of the sample through hole 74 is selected to reduce gas bubbling and to provide for venting of gas. For example, a volume ratio of 2 to 1 or more preferably 4 to 1, or most preferably 6 to 1 is used. In the embodiments of FIG. 3 and FIG. 4, the relatively larger vent hole volume 80 serves to anchor the permeable polymer or permeation layer 82 within the laminated structure 30. This property is especially advantageous if the permeable polymer or permeation layer 82 swells upon contact with fluids. Further, the structures of FIG. 3 and FIG. 4 have a relatively larger buffering capacity compared to structures not containing that volumetric ratio. Optionally, in the structures of FIG. 3 and FIG. 4, the planar support 78, 78A may be formed of relatively thicker, relatively rigid nonsheet-like material. For example, a laminated 30 may be affixed to another structure, such as a molded flow cell, or other structure formed of acrylic, plastic, metal or the like.

Figure 5:
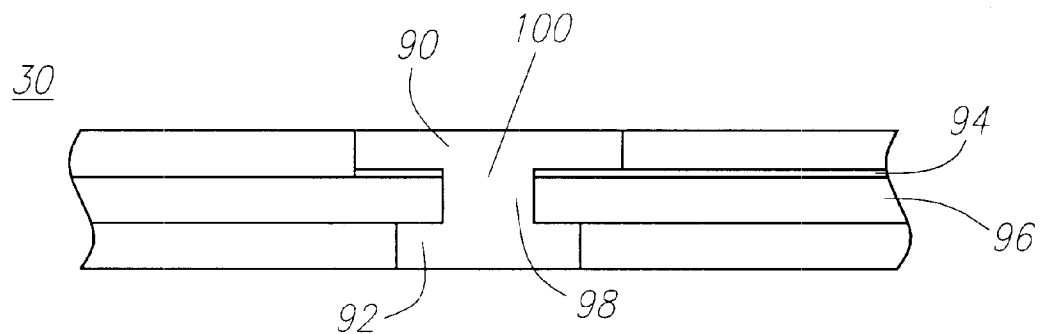
FIG. 5 is a cross-sectional view of a multilayer structure having a sample through hole with a lateral dimension greater than the lateral dimension of the vent through hole, which in turn is larger than the lateral dimension of the electrode through region.
Figure 6:
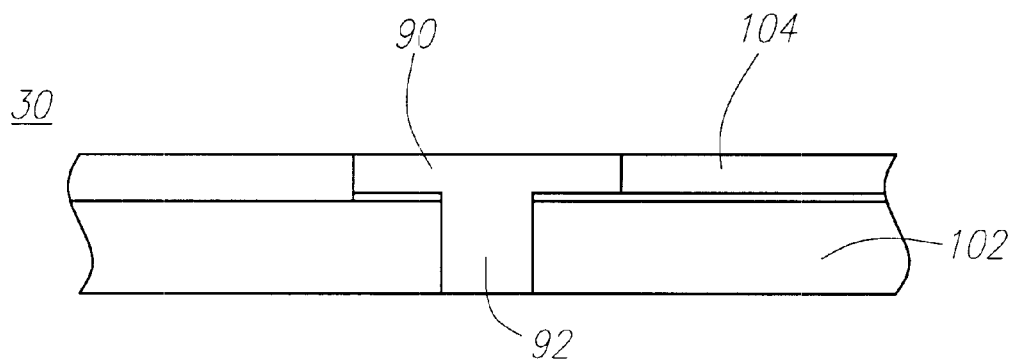
FIG. 6 is a cross-sectional view of a multilayer structure in which the lateral dimension of the sample through hole is greater than the lateral dimension of the electrode through region and vent through hole.

FIG. 5 and FIG. 6 show embodiments in which a laminated structure 30 has a sample through hole 90 which is wider than the lateral width of the vent hole 92. In FIG. 5, the electrode 94 is disposed upon a planar support 96 which has a vent through hole 98 of substantially the same lateral dimension as the electrode through region 100. The lateral dimension of the vent hole 92 in FIG. 5 is greater than the lateral dimensions of the vent hole 98 in the planar support 96 and the electrode through region 100. FIG. 6 utilizes a planar support 102 which is relatively thicker, e.g., twice as thick, as the planar sample support 104.

Figure 7:
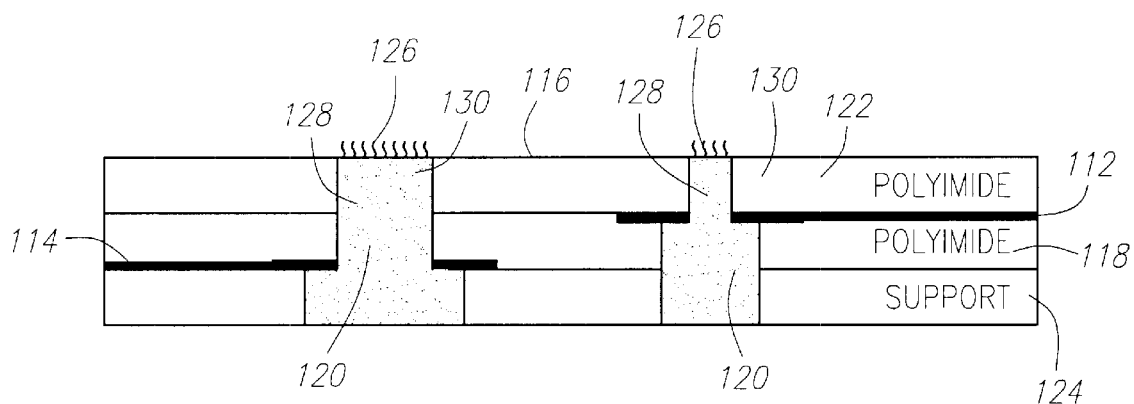
FIG. 7 is a cross-sectional view of a multilayer, laminated structure having a first electrode and second electrode at different distances from the sample surface of the system.

FIG. 7 is a cross-sectional diagram of a laminated structure 110 in which a first electrode 112 and a second electrode 114 are at different distances from the structure external surface 116 which is adapted to receive a sample. In the embodiment shown in FIG. 7, an intervening planar support layer 118 serves as the offset structure between the first layer electrode 112 and second layer electrode 114. The intervening planar support layer 118 includes intervening through holes 120. The left most intervening through hole 120 is disposed on the sample side of the laminated structure 110, whereas the intervening through hole 120 on the right hand side is disposed as a vent through hole. A planar sample support 122 is disposed adjacent the intervening planar support layer 118, and sandwiches the first layer electrode 112. The second planar support layer 124 is disposed adjacent the intervening planar support layer 118, having the second layer electrode 114 sandwiched therebetween. As shown in previous figures, probes 126 are disposed on or in the permeation layer 128 which fills at least the sample through hole regions 130, and on the left-hand side of FIG. 7, the intervening through hole 120.

Figure 8:
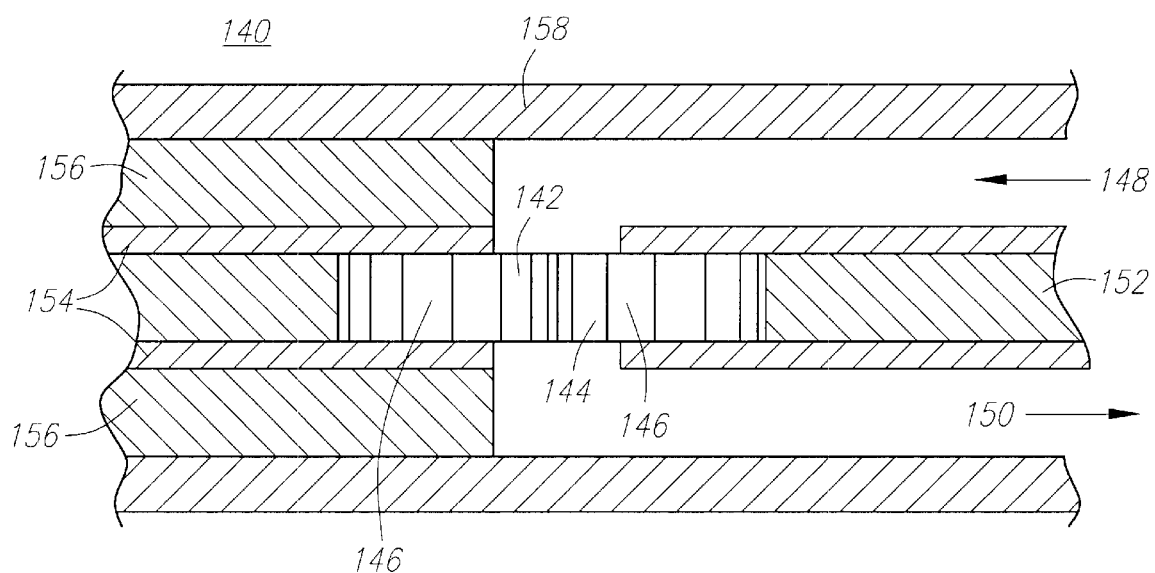
FIG. 8 is a cross-sectional view of a multilayer, laminated structure including an integrated active device, namely, a pump.

FIG. 8 is a cross-sectional view of a laminated structure 140, which includes a microminiaturized structure 142 disposed on, in or adjacent to the laminated structure 140. FIG. 8 shows a fluidic pump 144 comprising gears 146 shown in meshed relationship. The gears 146 are preferably rotated relative to each other through application of a rotational force, such as supplied by oscillating magnetic fields applied to the magnet disposed within the gears 146. A fluid inlet 148 and fluid outlet 150 provide a fluid path in communication with the fluidic pump 144. An adjacent layer 152 and lateral layers 154 provide containment for the gears 146. The fluid inlet 148 and fluid outlet 150 are defined by the void or space created by supports 156 and exterior layers 158. While a fluidic pump 144 is shown in FIG. 8, other microminiaturized structures 142 consistent with the goals and objects of this invention may be utilized. For example, other microminiaturized structures 142 may include microminiaturized machines, other linear motion devices, valves, actuators, or other micro fluidics components. See, e.g., Dewa, Andy et al. "Design and Implementation of CIGA Fabricated Self-Ringing In-Line Gear Pumps," Solid State Sensor and Actuator Workshop, Hilton Heid, S. C., Jun. 2–6, 1996.

Figure 9:
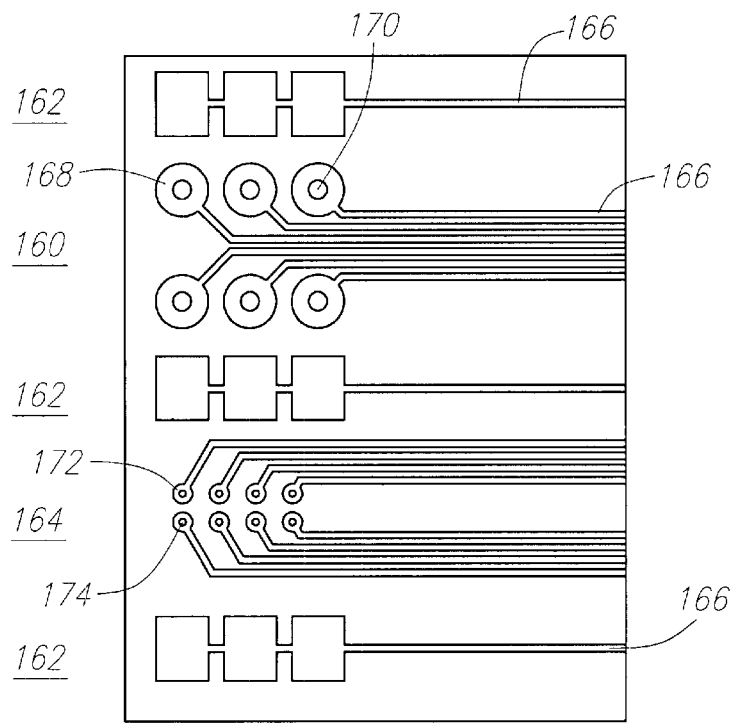
FIG. 9 is a plan view of an electrode pattern adapted for complexity reduction and biological assays, including return electrodes.

FIG. 9 shows a plan view of a electrode or metallization pattern for a device including a complexity reduction and/or sample preparation region 160, return electrode regions 162 and assay region 164. Traces 166 are shown leaving the various regions 160, 162, 164 for connection external to the device or to other electronic components. The complexity reduction and/or sample preparation region 160 includes traces 166 which include round electrodes 168 having electrode through regions 170 there through. The return electrodes 162 are connected by trace 166. The assay region 164 has traces 166, which terminate in enlarged electrode regions 172 and have electrode through regions 174 therethrough.

Figure 10:
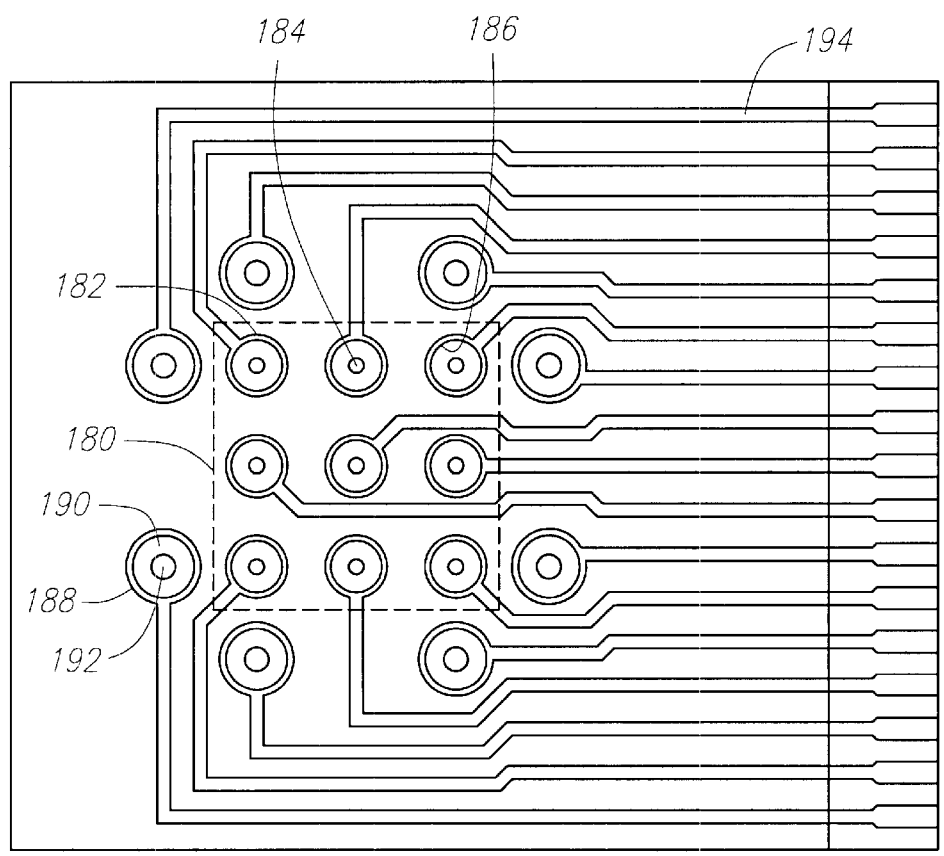
FIG. 10 is a plan view of patterned planar electrodes and planar sample support for a 3×3 assay array with surrounding return electrodes.

FIG. 10 shows a plan view of a 3×3 array of diagnostic assay sites, surrounded by return electrodes. The array 180 (encircled by dashed lines) shows an underlying trace 182 formed in a circular pattern having an electrode through region 184 therethrough. A planar sample support is disposed above the electrode traces 132 and is shown by the planar sample support interior edge 186. The counter electrodes 188 have a larger diameter than the assay sites, preferably at least 2:1, more preferably 3:1. The circular electrode 190 terminates at its interior edge in the electrode through region 192. Optionally, the electrode edge may terminate away from the through region of the support, as in an annulus, so as to leave a ring gap of support between the metal and the through hole. Traces 194 connected circular electrode regions 182, 190 to electronic devices or connectors (not shown). Optionally, circuit on flex technology may advantageously permit the positioning of electronic components on the laminated structure 30.

The laminated structures are preferably formed by methods, which permit the high yield, low cost manufacturing of high quality devices. The various holes, such as vent holes, sample through holes and electrode through regions may be formed through any known technique consistent with the objects and goals of this invention. For example, microminiaturized drills may form holes as small as 38 mils, while laser drilled holes may be as small as 4 mils, or photolithographically patterned holes may be formed to substantially 1 mil. Generally, utilizing current technology, the thinnest sheets permit the formation of the smallest diameter holes. Optionally, chemical etching may be utilized to remove debris from the holes. This technique is particularly advantageous after laser drilling of holes, so as to reduce or remove previously ablated materials. After the electrodes are patterned on the support, and various layers are fabricated, the laminated or composite structure 30 is adhered together. Generally, it is desirable to have minimal or no squeeze out of adhesive to avoid nonuniformity in terms of exposed electrode area. In one embodiment, relatively larger holes are first formed, and then relatively smaller holes are drilled through the larger holes. Alternately, the supports including vents and holes may be formed first, and then aligned, such as through optical alignment, prior to the setting of the adhesive.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

What is claimed is:

1. A multilayer, laminated device for performing fluidic operations, the device comprising:

a first exterior support layer, an adjacent layer disposed in laminated relationship with a portion of the exterior support layer, a second exterior support layer disposed in laminated relationship with a portion of the adjacent layer, and a fluidic pump disposed in the adjacent layer comprising:

a first gear rotationally mounted to the adjacent layer, the first gear having a magnet contained therein;

a second gear rotationally mounted to the adjacent layer, the second gear having a magnet contained therein, the second gear being engaged with the first gear in a meshed relationship.

2. The device of claim 1 for performing fluidic operations wherein the fluidic pump is driven by oscillating magnetic fields applied to the magnets in the first and second gears.

3. The device of claim 1 for performing fluidic operations further including a fluid inlet to the fluidic pump.

4. The device of claim 3 for performing fluidic operations wherein the fluid inlet is defined by a gap between the exterior support and the adjacent layer.

5. The device of claim 3 further including a fluid outlet to the fluidic pump.

* * * * *